(12) United States Patent
Ishii et al.

(10) Patent No.: US 8,749,626 B2
(45) Date of Patent: Jun. 10, 2014

(54) SAFE NURSING SYSTEM AND METHOD FOR CONTROLLING SAFE NURSING SYSTEM

(75) Inventors: Hiromoto Ishii, Kyoto (JP); Makoto Miyazaki, Otsu (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/876,304

(22) PCT Filed: Jul. 15, 2011

(86) PCT No.: PCT/JP2011/066235
§ 371 (c)(1),
(2), (4) Date: Mar. 27, 2013

(87) PCT Pub. No.: WO2012/043020
PCT Pub. Date: Apr. 5, 2012

(65) Prior Publication Data
US 2013/0215248 A1    Aug. 22, 2013

(30) Foreign Application Priority Data
Sep. 29, 2010 (JP) ................................. 2010-219192

(51) Int. Cl.
*H04N 7/18* (2006.01)
(52) U.S. Cl.
CPC ..................................... *H04N 7/188* (2013.01)
USPC .......................................................... 348/77
(58) Field of Classification Search
CPC ................................. H04N 7/18; H04N 7/188
See application file for complete search history.

(56) References Cited

U.S. PATENT DOCUMENTS

| 2006/0145874 A1 | 7/2006 | Fredriksson et al. |
| 2009/0044334 A1* | 2/2009 | Parsell et al. ..................... 5/424 |
| 2009/0187112 A1* | 7/2009 | Meir et al. ..................... 600/534 |

FOREIGN PATENT DOCUMENTS

| JP | 2004-096457 A | 3/2004 |
| JP | 2005-128967 A | 5/2005 |
| JP | 2006-175082 A | 7/2006 |
| JP | 2006-522959 A | 10/2006 |
| JP | 2009-077908 A | 4/2009 |
| KR | 2007003751 A | * 1/2007 |

OTHER PUBLICATIONS

Official Communication issued in International Patent Application No. PCT/JP2011/066235, mailed on Aug. 9, 2011.

* cited by examiner

*Primary Examiner* — Sath V Perungavoor
*Assistant Examiner* — Kate Luo
(74) *Attorney, Agent, or Firm* — Keating & Bennett, LLP

(57) ABSTRACT

A safe nursing system that monitors movement of a patient on a bed includes a control unit and an image capturing unit disposed in a position from which an image including a side of a top surface of the bed can be captured. The control unit obtains image data captured by the image capturing unit; specifies feature points in an image of the patient in the obtained image data, and calculates a value of a predetermined index of the feature points used to determine a predetermined movement in the patient; sets a predetermined condition to determine the predetermined movement based on a region of the bed in the obtained image data; determines the predetermined movement based on the calculated value and the set predetermined condition; and outputs information indicating that the patient has performed the predetermined movement under the condition that the predetermined movement has been determined to have been performed.

8 Claims, 9 Drawing Sheets

FIG. 7

| CONDITION | MOVEMENT | | | | | |
|---|---|---|---|---|---|---|
| | MOVING THE HEAD | ATTEMPTING TO RISE | RISING | TURNING OVER | ATTEMPTING TO DESCEND | DESCENDING |
| POOR | CAUTION | WARNING | WARNING | CAUTION | WARNING | WARNING |
| FAIR | NORMAL ALERT | CAUTION | CAUTION | NORMAL ALERT | CAUTION | WARNING |
| GOOD | — | — | — | — | NORMAL ALERT | CAUTION |

SAFE NURSING SYSTEM AND METHOD FOR CONTROLLING SAFE NURSING SYSTEM

BACKGROUND OF THE INVENTION

1. Field of the Invention

The present invention relates to safe nursing systems and methods for controlling safe nursing systems, and particularly relates to safe nursing systems and methods for controlling safe nursing systems that monitor the movement of a patient on a bed.

2. Description of the Related Art

In the past, an apparatus such as a biological information monitor has been used to measure vital signs such as blood pressure, body temperature, a cardiograph, arterial oxygen saturation, and breathing rate in order to monitor the biological state of a patient in a hospital, a household, or the like. When the measurement has returned an abnormal value, the apparatus or a remote central management apparatus to which the apparatus is connected visually and auditorily alerts a doctor or a nurse.

However, a situation such as where the patient has fallen out of his or her bed cannot be completely prevented simply by checking vital signs.

The following is an example of a sensor serving as a safe nursing system for preventing such falls from a bed. For example, an infrared sensor, an image sensor, or a beam sensor is an example of a sensor that does not come into contact with the patient. On the other hand, a floor-based foot sensor or a mat sensor placed under a sheet is an example of a sensor that comes into contact with the patient. A clip sensor is an example of a sensor affixed to the patient.

Such safe nursing systems can, within the sensing range of the sensors, mechanically convert the movement of the patient, such as whether or not the patient is on his or her bed, into simplified patterns and notify a caregiver (a nurse) thereof.

However, such safe nursing systems have had problems in that finer movements of the patient (coughing, rolling over, and so on) cannot be recognized, notifications are made without determining that the patient has moved, notifications are made after the patient has moved (for example, after the patient has fallen out of his or her bed), and so on.

In response to such problems, a rising monitoring method and apparatus has been proposed as a safe nursing system. This method and apparatus set a monitoring region for determining whether a subject (also called a "patient" hereinafter) has risen from his or her bed, use a camera to capture an image of a space from the side of the bed that includes the monitoring region, and determine that the subject is exhibiting rising behavior in the case where the size of a subject image region that fits within the monitoring region in the captured image has become greater than or equal to a predetermined value (see JP 2006-175082A).

However, with the method and apparatus according to JP 2006-175082A, the images are captured from the side, and there is a problem in that errors have increased due to nurses entering the captured image. Furthermore, depending on the installation location, the camera has also interfered with the nurses' work.

In addition, because the image is captured from the side, there is a problem in that it is difficult to detect the patient moving toward a side of the bed, which is an indication that the patient will fall out of the bed. Furthermore, there is a problem that in the case where the patient does not enter the monitoring region, such as in a case where the patient does not rise and instead rolls to the side and falls out of the bed, the patient's movement cannot be detected at all.

In addition, because rising behavior is determined based on the size of the patient's image region, there is a problem in that errors will occur in the determination results depending on the manner in which the patient rises (rising behavior and how far the patient's body enters the monitoring region), differences in body shape among patients, and so on.

SUMMARY OF THE INVENTION

In order to solve the problems stated above, preferred embodiments of the present invention provide a safe nursing system and a method for controlling a safe nursing system that avoid interfering with a caregiver's care.

Another preferred embodiment of the present invention provides a safe nursing system and a method for controlling a safe nursing system that more accurately determines a level of danger of a patient's movement.

Another preferred embodiment of the present invention provides a safe nursing system and a method for controlling a safe nursing system that make errors caused by differences in manners of movement and patient body shapes less likely to occur indetermination results.

A safe nursing system according to a preferred embodiment of the present invention includes a system that monitors movement of a patient on a bed. The safe nursing system includes a control unit and an image capturing unit disposed in a position from which an image including a side of a top surface of the bed can be captured.

The control unit preferably includes an image capturing control unit that obtains image data captured by the image capturing unit; a calculation unit that specifies feature points in an image of the patient in the image data obtained by the image capturing control unit and calculates a value of a predetermined index of the feature points used to determine a predetermined movement in the patient; a setting unit that sets a predetermined condition to determine the predetermined movement based on a region of the bed in the image data obtained by the image capturing control unit; a determination unit that determines the predetermined movement based on the value calculated by the calculation unit and the predetermined condition set by the setting unit; and an output unit that outputs information indicating the patient has performed the predetermined movement under the condition that the determination unit has determined that the predetermined movement has been performed.

Preferably, the image capturing unit is disposed in a position from which an image can be captured from the direction of the head area of the patient. Further preferably, the calculation unit calculates a value of the predetermined index for the feature points included in a region of the head area from among the specified feature points.

Preferably, the calculation unit calculates coordinates of the feature points as the value of the predetermined index. The setting unit sets, as the predetermined condition, a condition for a predetermined border to determine whether a plurality of the coordinates indicate the predetermined movement in the patient.

Further preferably, the determination unit determines the predetermined movement based on whether or not an extent to which the coordinates calculated by the calculation unit have exceeded the predetermined border set by the setting unit has exceeded a predetermined threshold.

Further preferably, the calculation unit further calculates a movement direction of the feature points as the value of the predetermined index. The determination unit determines the predetermined movement based on whether or not an extent to which the coordinates calculated by the calculation unit have approached the predetermined border has exceeded a predetermined threshold.

Preferably, the setting unit sets the predetermined condition in accordance with a pre-set specification method based on the position of a side or an end of the bed.

A control method for a safe nursing system according to another preferred embodiment of the present invention includes a control unit and an image capturing unit disposed in a position from which an image including a side of a top surface of the bed can be captured and that monitors a movement of a patient on a bed.

In this control method, the control unit executes a step of obtaining image data captured by the image capturing unit; a step of specifying feature points in an image of the patient in the obtained image data and calculating a value of a predetermined index of the feature points used to determine a predetermined movement in the patient; a step of setting a predetermined condition to determine the predetermined movement based on a region of the bed in the obtained image data; a step of determining the predetermined movement based on the calculated value and the set predetermined condition; and a step of outputting information indicating that the patient has performed the predetermined movement under the condition that the predetermined movement has been determined to have been performed.

According to a preferred embodiment the present invention, the image capturing unit is disposed in a position from which an image including the side of the top surface of the bed can be captured, and thus does not capture images from the side of the bed. Accordingly, it is possible to provide a safe nursing system and a method for controlling a safe nursing system that avoid interfering with a caregiver's care.

Furthermore, because both sides of the top surface of the bed are also captured, a reference value based on the sides can be set. Accordingly, it is possible to provide a safe nursing system and a method for controlling a safe nursing system that more accurately determines a level of danger of a patient's movement.

In addition, the movement of the patient is determined not using a range, but by using a plurality of points. Accordingly, it is possible to provide a safe nursing system and a method for controlling a safe nursing system that make errors caused by differences in manners of movement and patient body shapes less likely to occur in determination results.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 7 is a diagram used to set predetermined movements and alert levels on a patient-by-patient basis according to a preferred embodiment of the present invention.

DETAILED DESCRIPTION OF THE PREFERRED EMBODIMENTS

Figure 1:
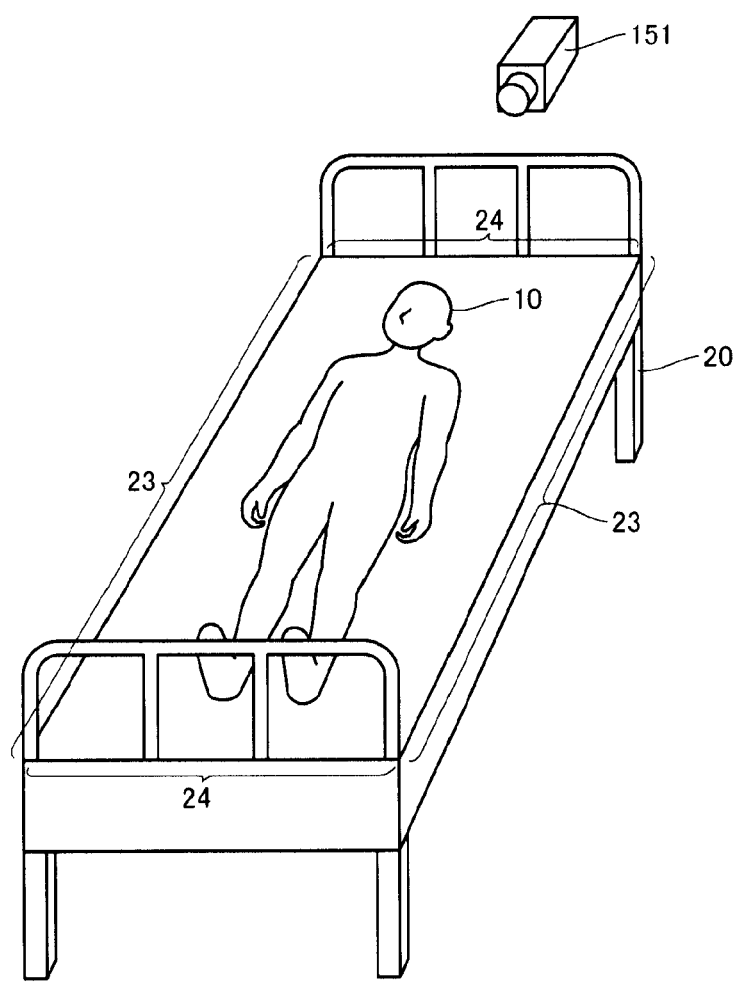
FIG. 1 is a diagram illustrating an installation position of a camera in a safe nursing system according to a preferred embodiment of the present invention.

Hereinafter, preferred embodiments of the present invention will be described in detail with reference to the drawings. Note that identical or corresponding elements in the drawings will be given the same reference numerals, and descriptions thereof will not be repeated.

FIG. 1 is a diagram illustrating an installation position of a camera 151 in a safe nursing system according to a preferred embodiment of the present invention. As shown in FIG. 1, the camera 151 of the safe nursing system according to the present preferred embodiment is disposed in a position from which an image of a patient 10 on a bed 20 can be captured from the direction of the patient's head area.

Note that as long as the camera 151 is disposed in a position in which an image including side ends (hereinafter referred to as "sides") 23 and 23 of the upper surface of the bed 20 can be captured, the camera 151 is not limited to a position from which an image of the patient 10 can be captured from the direction of the patient's head area. For example, the camera 151 may be disposed in a position from which an image of the patient 10 can be captured from the direction of the patient's feet.

Meanwhile, it is preferable for the camera 151 to be disposed in a position from which an image including lengthwise ends (hereinafter referred to as "ends") 24 and 24 of the top surface of the bed 20 can be captured.

In addition, the "patient 10" includes a person who needs to be monitored by another person, such as a subject receiving care from a caregiver such as a doctor or a nurse in a hospital or the like, as well as a subject receiving assistance from a caregiver in an assisted-living facility or the like.

Figure 2:
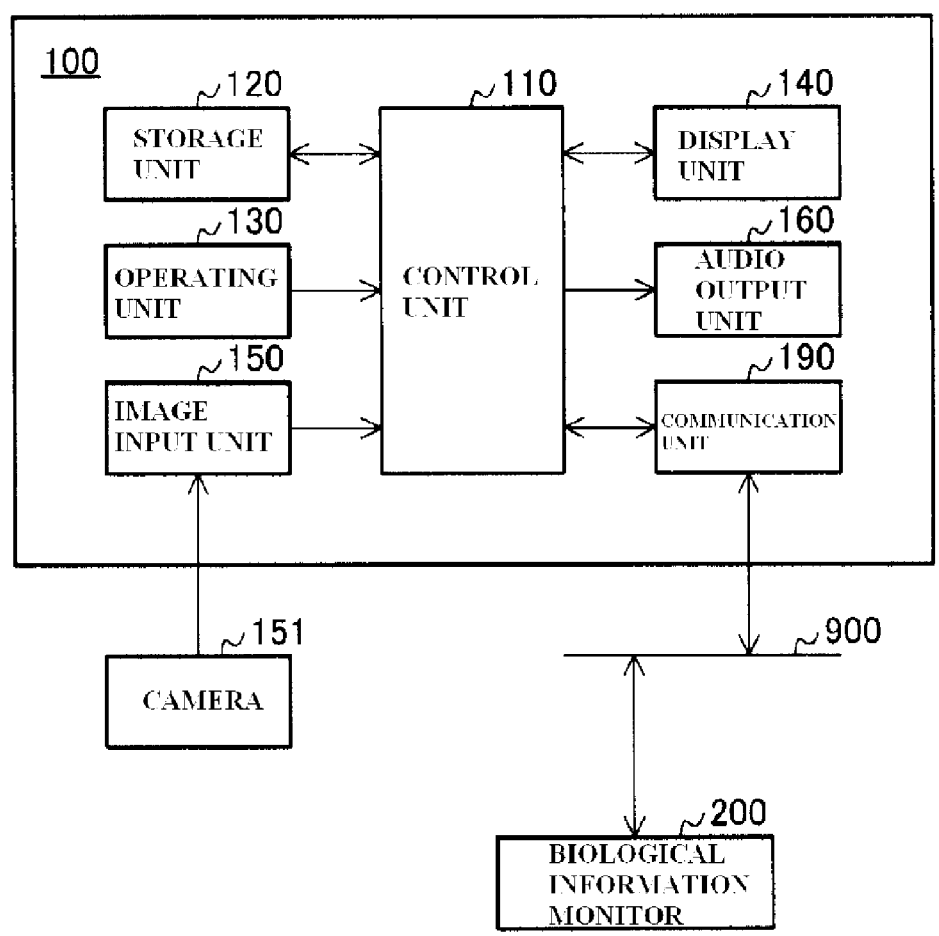
FIG. 2 is a block diagram illustrating the overall configuration of a control apparatus in a safe nursing system according to a preferred embodiment of the present invention.

FIG. 2 is a block diagram illustrating the overall configuration of a control apparatus 100 in the safe nursing system according to the present preferred embodiment. As shown in FIG. 2, the control apparatus 100 preferably includes a control unit 110, a storage unit 120, an operating unit 130, a display unit 140, an image input unit 150, an audio output unit 160, and a communication unit 190.

The control unit 110 includes a CPU (central processing unit) and other auxiliary circuits. The control unit 110 is programmed to control the various elements of the control apparatus 100, execute predetermined processes in accordance with programs and data stored in the storage unit 120, process data inputted from the operating unit 130, the image input unit 150, and the communication unit 190, store processed data in the storage unit 120, display processed data in the display unit 140, output processed data through the audio output unit 160 as audio, and output processed data from the communication unit 190, for example.

The storage unit 120 includes a RAM (random access memory) used as a work region required by the control unit 110 to execute programs, and a ROM (read-only memory) to store basic programs to be executed by the control unit 110. A magnetic disk (an HD (hard disk), an FD (flexible disk)), an optical disc (a CD (compact disc), a DVD (digital versatile disc), a BD (Blu-ray disc)), a magneto-optical disc (MO), or a semiconductor memory (a memory card, an SSD (solid state drive)), or the like may be used as a storage medium in an auxiliary storage apparatus to complement the storage region of the storage unit 120.

The operating unit 130 includes a keyboard and a mouse, and sends operating signals indicating operations performed by a user to the control unit 110. Instead of or in addition to the keyboard and the mouse, the operating unit 130 may include another operating device, such as a touch panel.

The display unit 140 includes a display (for example, an LCD (liquid-crystal display)). The display unit 140 displays a predetermined image in the display under the control of the control unit 110.

The audio output unit 160 includes a speaker. The audio output unit 160 outputs predetermined audio from the speaker under the control of the control unit 110.

The image input unit 150 passes image data inputted from the camera 151 to the control unit 110, as well as stores the image data in the storage unit 120, displays the image data as images in the display unit 140, and so on under the control of the control unit 110.

The communication unit 190 sends information from the control unit 110 to other apparatuses (for example, in the present preferred embodiment, a biological information monitor 200) via a network 900, and receives and exchanges information sent via the network from another apparatus with the control unit 110. Although the network 900 is preferably a LAN (local area network) in a hospital in the present preferred embodiment, the network 900 is not limited thereto, and may be another type of network, such as a network constructed over the Internet.

The biological information monitor 200 measures biological information such as blood pressure, heart rate, and so on using probes attached to the patient, and displays the measured biological information, sends the biological information to other apparatuses via the network 900, and so on.

The camera 151 converts an image captured within an image capturing range into image data, and in the present preferred embodiment, sends the image data to the image input unit 150 of the control apparatus 100. In the present preferred embodiment, the camera 151 captures moving images. However, the image is not limited thereto, and the camera 151 may capture still images in sequence over short time intervals (for example, about every 0.1 seconds).

Figure 3:
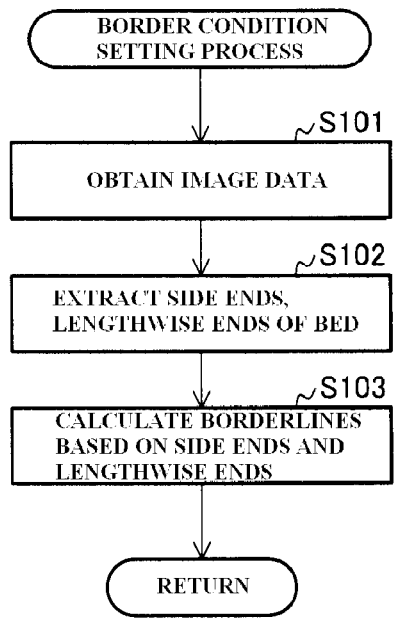
FIG. 3 is a flowchart illustrating the flow of a border condition setting process executed by the control apparatus according to a preferred embodiment of the present invention.

FIG. 3 is a flowchart illustrating the flow of a border condition setting process executed by the control apparatus 100 according to the present preferred embodiment. As shown in FIG. 3, in step S101, the control unit 110 acquires, from the storage unit 120, image data that has been inputted to the image input unit 150 from the camera 151 and stored in the storage unit 120.

Next, in step S102, the control unit 110 extracts the sides 23 and 23 and ends 24 and 24 of the bed 20 from the image of the bed 20 displayed based on the image data acquired in step S101.

Figure 4:
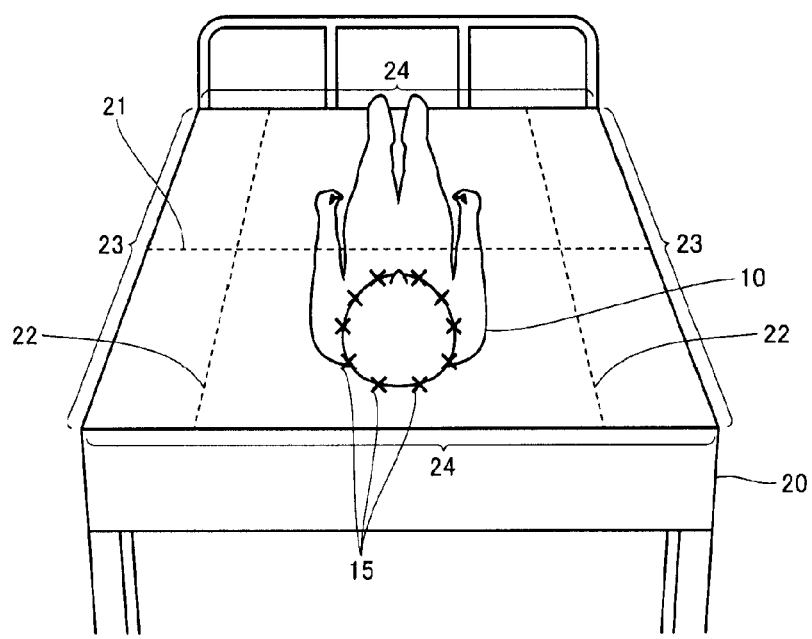
FIG. 4 is a first diagram illustrating an image captured by a camera connected to the control apparatus according to a preferred embodiment of the present invention.

FIG. 4 is a first diagram illustrating an image captured by the camera 151 connected to the control apparatus 100 according to the present preferred embodiment. As shown in FIG. 4, the patient 10 and the bed 20 are included in the image illustrated here. However, it is preferable that the patient 10 is not present when the border condition setting process shown in FIG. 3 is executed.

As illustrated in FIG. 1, the camera 151 is disposed in a position in which both of the sides 23 and 23 of the top surface of the bed 20 can be captured from the direction of the patient's head area when the patient 10 is lying on the bed 20. Accordingly, an image of the top surface of the bed 20 is included in the captured image as an approximately trapezoidal shape. In the case where the camera 151 is disposed along a center line in the lengthwise direction of the bed 20 facing toward the center line, an image of the top surface of the bed 20 is included in the captured image as an approximately isosceles trapezoidal shape.

Meanwhile, in the case where the patient 10 is lying on the bed 20, the image of the patient 10 is included in the captured image so that the patient's head is toward the lower base of the trapezoid and the patient's feet are toward the upper base of the trapezoid that corresponds to the shape of the upper surface of the bed 20.

The legs of the trapezoid correspond to the sides 23 and 23 of the upper surface of the bed 20, whereas the upper base and lower base of the trapezoid correspond to the ends 24 and 24 of the upper surface of the bed 20.

Returning to FIG. 3, in step S103, the control unit 110 calculates borderlines 21 and 22 under a predetermined condition to determine a predetermined movement in the patient 10, based on the sides 23 and 23 and the ends 24 and 24 extracted in step S102. After step S103, the control unit 110 returns from the process being executed to the process that called this process.

As will be described below with reference to FIG. 7, moving the head, attempting to rise, rising, turning over, attempting to descend (from the bed 20), and descending (from the bed 20) are examples of predetermined movements of the patient 10.

Note that moving the head can be taken as an indication that the patient is attempting to rise, an indication that the patient is rising, and an indication that the patient is turning over. Attempting to rise can be taken as an indication that the patient is rising. Turning over can be taken as an indication that the patient is attempting to descend from the bed 20 and as an indication that the patient is descending from the bed 20. Attempting to descend from the bed 20 can be taken as an indication that the patient is descending from the bed 20.

In other words, the patient 10 can move in the following sequence: (1) moving the head, (2) attempting to rise, (3) rising, (4) attempting to descend from the bed 20, and (5) descending from the bed 20. There are cases where the patient 10 moves in other sequences as well. The patient 10 can also move in the following sequence: (1) moving the head, (2) attempting to descend from the bed 20, and (3) descending from the bed 20.

In the case where the patient has safely descended from the bed 20 under his or her own will, the movement of descending from the bed 20 is simply a movement of descending from the bed 20. However, a case where the patient is not moving under his or her own will and a case where the patient has not descended safely correspond to the patient falling from the bed 20. In other words, the patient descending from the bed 20 includes both the patient simply descending from the bed 20 and the patient falling from the bed 20.

Meanwhile, in the present preferred embodiment, a condition in which no less than a predetermined percentage of feature points 15 assigned to the head area of the patient 10 have passed a borderline is taken as the predetermined condition. It is determined that the predetermined movement has been made in the case where the predetermined condition has been met.

An algorithm such as SIFT (scale-invariant feature transform) and SURF (speeded-up robust features) can be used as the algorithm that extracts the feature points of an object (in the present preferred embodiment, the patient 10).

However, the predetermined condition is not limited thereto, and a condition in which no less than a predetermined percentage of motion vectors of the feature points 15 of the head area of the patient 10 have passed a borderline may be used as the predetermined condition. Vectors indicating the amount and direction in which the feature points 15 have moved between a predetermined number of frames in the past and the current frame serve as the motion vectors of the feature points 15.

An algorithm such as the SIFT and SURF can be used as the algorithm that calculates the motion vectors of the feature points of an object (in the present preferred embodiment, the patient 10).

A condition in which a cumulative percentage of the motion vectors of the feature points 15 of the head area of the patient 10 are passing a borderline within a predetermined amount of time is greater than or equal to a predetermined percentage may be used as the predetermined condition.

A condition in which a percentage of the motion vectors of the feature points 15 of the head area of the patient 10 that are approaching a borderline is greater than or equal to a predetermined percentage may be used as the predetermined condition.

A condition in which a cumulative percentage of the motion vectors of the feature points 15 of the head area of the patient 10 that are approaching a borderline within a predetermined amount of time is greater than or equal to a predetermined percentage may be used as the predetermined condition.

Although a borderline is preferably used in the aforementioned predetermined conditions, a long, thin border region may be used instead, for example.

Alternatively, a condition that does not use a borderline may be used as the predetermined condition. For example, the predetermined condition may be a condition in which the percentage of the feature points 15 of the head area of the patient 10 whose movement amounts (that is, the magnitudes of the motion vectors) are greater than or equal to a predetermined value (for example, about 20 cm) is greater than or equal to a predetermined percentage.

The predetermined condition may be a condition that the percentage of the feature points 15 of the head area of the patient 10 whose movement directions (that is, the direction of the motion vectors) correspond to a direction moving away from the bed 20 or a direction moving toward a side of the bed 20 is greater than or equal to a predetermined percentage.

The predetermined condition may be a condition that, in the case where the patient 10 is close to a side of the bed 20 (for example, within the range of a predetermined distance (for example, about 30 cm) from a side), the percentage of the feature points 15 of the head area of the patient 10 whose movement velocities (that is, the magnitudes of the motion vectors per unit of time) are greater than or equal to a predetermined value (for example, about 10 cm/second) is greater than or equal to a predetermined percentage.

Furthermore, although the aforementioned predetermined conditions discuss the feature points 15 of the head area, feature points of other areas (for example, the shoulders) may be used as well.

Furthermore, although the aforementioned predetermined conditions discuss percentages that are greater than or equal to a predetermined percentage, in the case where the number of the feature points 15 is a set number, a number that is greater than or equal to a predetermined number may be used.

Figure 5:
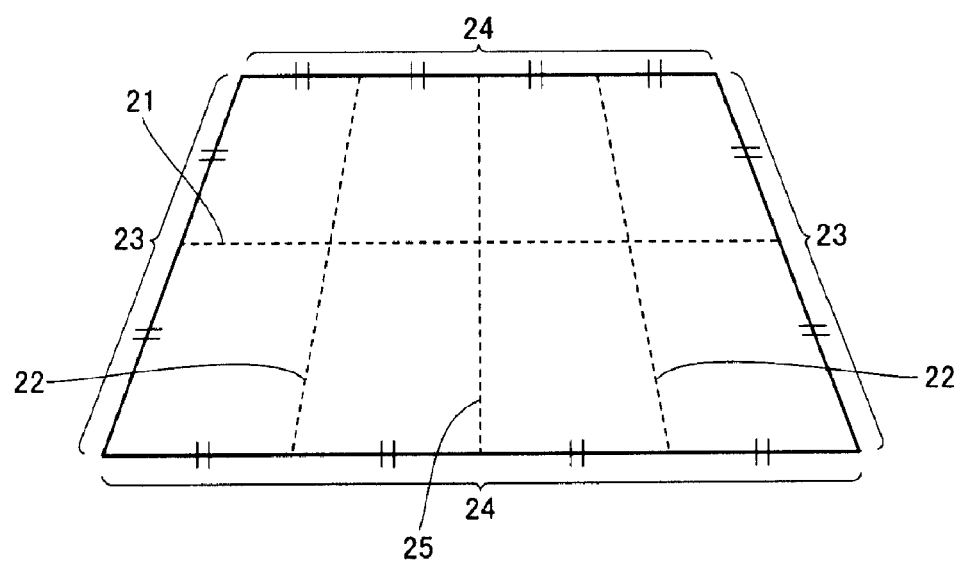
FIG. 5 is a diagram illustrating an example of a method for specifying a borderline under a predetermined condition to determine a predetermined movement in a patient according to a preferred embodiment of the present invention.

FIG. 5 is a diagram illustrating an example of a method for specifying a borderline under a predetermined condition to determine a predetermined movement in the patient according to the present preferred embodiment. As shown in FIG. 5, in the present preferred embodiment, a line within the trapezoidal shape that is an equal distance from the two ends 24 and 24 of the bed 20 is taken as a borderline 21 for predetermined conditions of moving the head, attempting to rise, and rising.

Meanwhile, lines within the trapezoidal shape that are equal distances from a center line 25 in the lengthwise direction of the bed and the respective sides 23 and 23 of the bed 20 are taken as borderlines 22 and 22 for predetermined conditions of turning over, attempting to descend from the bed 20, and descending from the bed 20.

Figure 6:
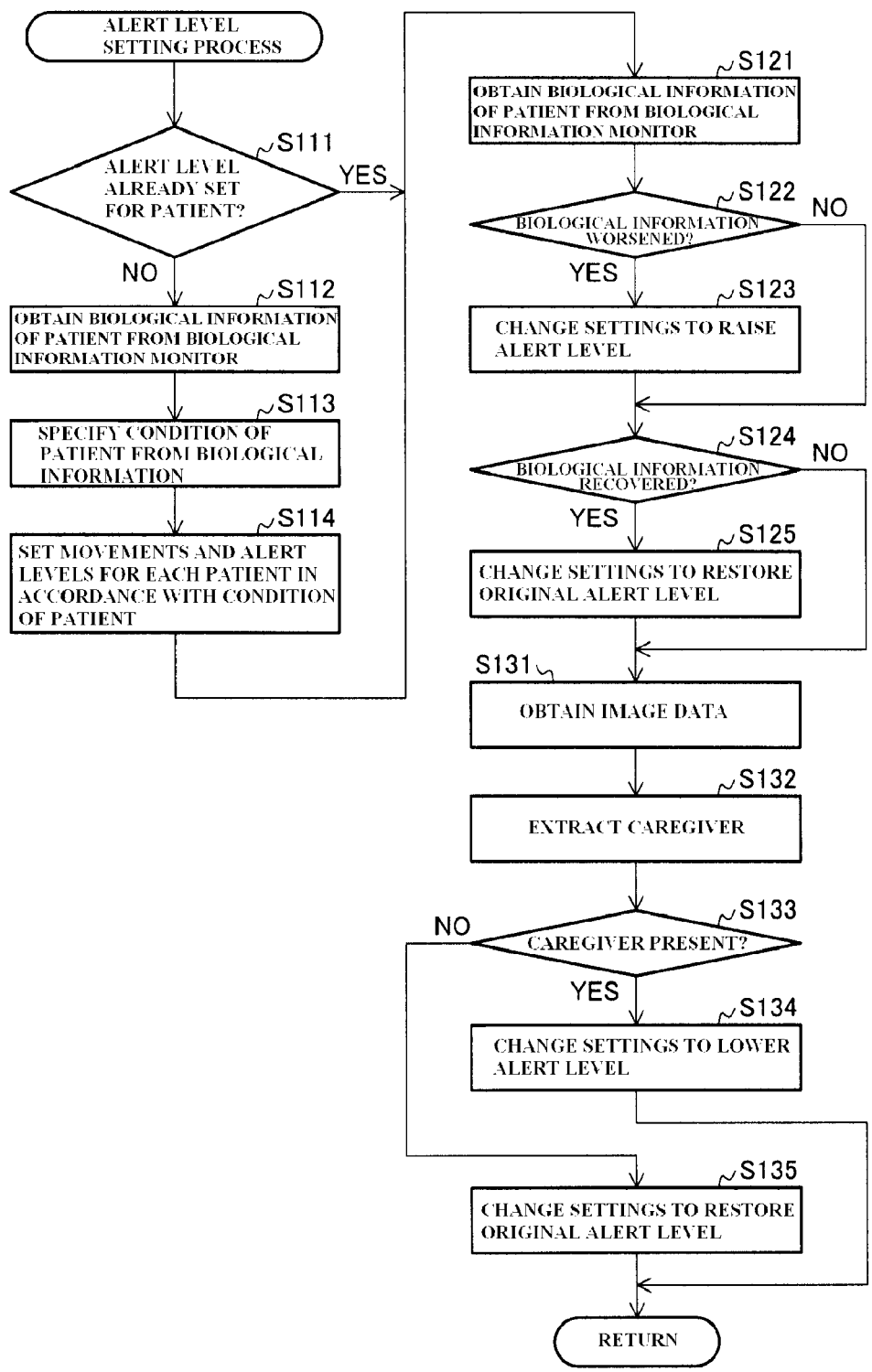
FIG. 6 is a flowchart illustrating the flow of an alert level setting process executed by the control apparatus according to a preferred embodiment of the present invention.

FIG. 6 is a flowchart illustrating the flow of an alert level setting process executed by the control apparatus 100 according to the present preferred embodiment. As shown in FIG. 6, the alert level setting process is a process that sets an alert level, indicating what type of alert to issue for a given movement, for each patient 10.

First, in step S111, the control unit 110 determines whether or not the patient 10 in question is a patient for whom alert levels have already been set. In the case where it has been determined that the patient has not already had an alert level set (the case of a determination of NO in step S111), in step S112, the control unit 110 obtains biological information of that patient 10 from the biological information monitor 200 via the network 900.

Next, in step S113, the control unit 110 specifies the condition of the patient 10 based on the biological information obtained in step S112. For example, the condition is specified as poor if the blood pressure is a-b or e-f. The condition is specified as fair if the blood pressure is b-c or d-e. The condition is specified as good if the blood pressure is c-d.

Then, in step S114, the control unit 110 specifies alert levels for the predetermined movements of each patient in accordance with the condition of the patient 10 specified in step S113.

FIG. 7 is a diagram used to set predetermined movements and alert levels on a patient-by-patient basis according to the present preferred embodiment. As shown in FIG. 7, in the case where the patient's condition has been specified as poor, the alert level is set to "caution" for moving the head and turning over, and is set to "warning" for attempting to rise, rising, attempting to descend (from the bed 20), and descending (from the bed 20).

In the case where the patient's condition has been specified as fair, the alert level is set to "normal alert" for moving the head and turning over, to "caution" for attempting to rise, rising, and attempting to descend (from the bed 20), and to "warning" for descending (from the bed 20).

In the case where the patient's condition has been specified as good, the alert level is set to "normal alert" for attempting to descend (from the bed 20) and to "caution" for descending (from the bed 20).

Here, "warning", "caution", and "normal alert" are alerts that are easier to be communicated to the caregiver, in that order. For example, with "warning", an alert that combines an alarm, an output of audio indicating details of the alert, flashes a lamp, and displays text indicating details of the alert is carried out, for example. With "caution", an alert the combines an output of audio indicating details of the alert and displays text indicating details of the alert is carried out, for example. With "normal alert", text indicating details of the alert is displayed, for example.

Returning to FIG. 6, after step S114 and in the case where it has been determined that an alert level has already been set for the patient (the case where a determination of YES has been made in step S111), in step S121, the control unit 110 obtains the biological information of that patient 10 from the biological information monitor 200 via the network 900.

In step S122, the control unit 110 determines whether or not the biological information of the patient 10 has worsened based on the biological information obtained in step S121.

For example, using the range of blood pressures for each condition described earlier in step S113 of FIG. 3, the biological information of the patient 10 is determined to have worsened in the case where a condition of "good", in which the blood pressure is c-d, has dropped to a condition of "fair", in which the blood pressure is b-c, d-e, and in the case where a condition of "fair", in which the blood pressure is c-d, d-e, has dropped to a condition of "poor", in which the blood pressure is a-b, e-f.

In the case where it has been determined that the biological information has worsened (the case where a determination of YES has been made in step S122), in step S123, the control unit 110 changes the setting for the patient 10 so as to raise the alert level set in step S114.

For example, the alert level for all movements is raised by one level. Specifically, movements for which the alert level is "normal alert" are raised to an alert level of "caution", and movements for which the alert level is "caution" are raised to an alert level of "warning".

After step S123, and in the case where it has been determined that the biological information has not worsened (the case where a determination of NO has been made in step S122), in step S124, the control unit 110 determines whether or not the biological information of the patient 10 has recovered based on the biological information obtained in step S121.

For example, using the range of blood pressures for each condition described earlier in step S113 of FIG. 3, the biological information of the patient 10 is determined to have recovered in the case where a condition of "fair", in which the blood pressure is b-c, d-e, has risen to a condition of "good", in which the blood pressure is c-d, and in the case where a condition of "poor", in which the blood pressure is a-b, e-f, has risen to a condition of "fair", in which the blood pressure is b-c, d-e.

In the case where it has been determined that the biological information has recovered (the case where a determination of YES has been made in step S124), in step S125, the control unit 110 changes the setting so as to restore the alert level, which was raised in step S123, to its original level.

For example, the alert level for all movements that was raised by one level is dropped by one level. Specifically, movements for which the alert level was raised to "caution" are reduced to an alert level of "normal alert", and movements for which the alert level was raised to "warning" are reduced to an alert level of "caution".

After step S125, and in the case where it has been determined that the biological information has not recovered (the case where determination of NO has been made in step S124), in step S131, the control unit 110 obtains, from the storage unit 120, the image data inputted to the image input unit 150 from the camera 151 and stored in the storage unit 120.

Next, in step S132, the control unit 110 extracts a caregiver from the image data obtained in step S131. In step S133, the control unit 110 determines whether or not the caregiver is present.

The extraction of the caregiver is carried out by, for example, extracting the caregiver's cap above an area determined to be a head area, and in the case where the caregiver's cap has been extracted, it is determined that the caregiver is present. Alternatively, the caregiver may be extracted by extracting a stethoscope whose position is moving.

Alternatively, a face included in the image expressed by the image data may be extracted using a facial recognition technique, and it may then be determined that a caregiver is present in the case where the extracted face and a registered face of the caregiver match.

In the case where it has been determined that the caregiver is present (the case where a determination of YES has been made in step S133), in step S134, the control unit 110 changes the setting for the patient 10 so as to lower the alert level set in step S114.

For example, the alert level for all movements is lowered by one level. Specifically, movements for which the alert level is "warning" are lowered to an alert level of "caution", and movements for which the alert level is "caution" are lowered to an alert level of "normal alert".

In the case where it has been determined that the caregiver is not present (the case where a determination of NO has been made in step S133), in step S135, the control unit 110 changes the setting so as to restore the alert level, which was lowered in step S134, to its original level.

For example, the alert level for all movements that was lowered by one level is raised by one level. Specifically, movements for which the alert level was lowered to "caution" are raised to an alert level of "warning", and movements for which the alert level was lowered to "normal alert" are raised to an alert level of "caution".

After step S134 and step S135, the control unit 110 returns from the process being executed to the process that called this process.

Figure 8:
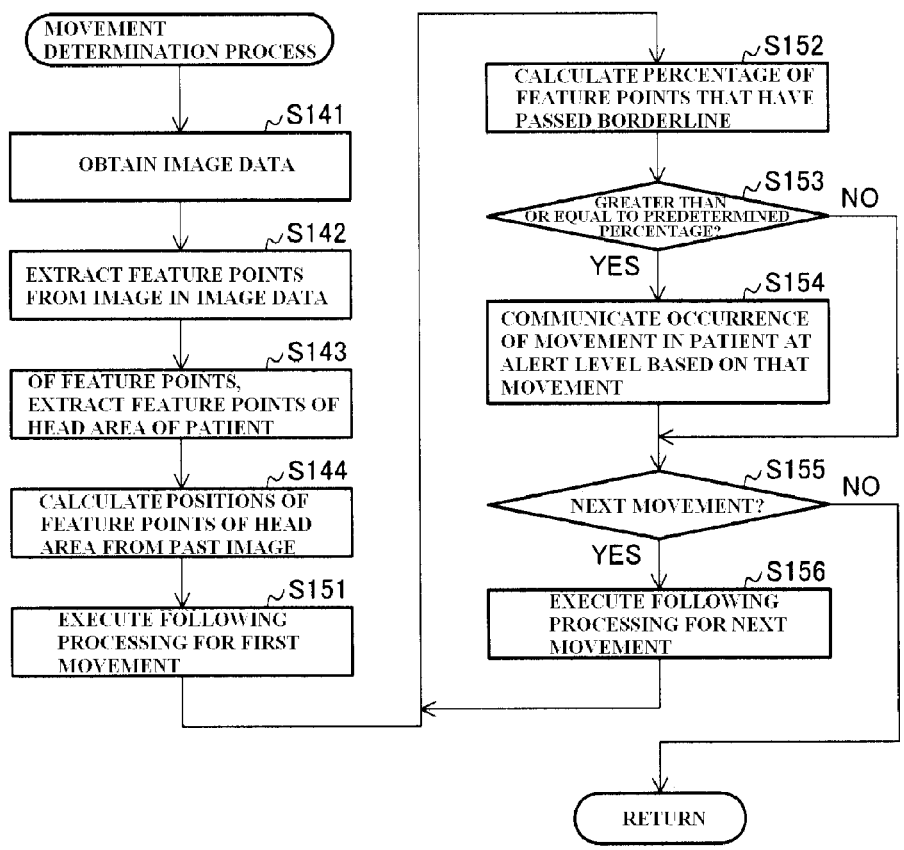
FIG. 8 is a flowchart illustrating the flow of a movement determination process executed by the control apparatus according to a preferred embodiment of the present invention.

FIG. 8 is a flowchart illustrating the flow of a movement determination process executed by the control apparatus 100 according to the present preferred embodiment. As shown in FIG. 8, in step S141, the control unit 110 acquires, from the storage unit 120, image data that has been inputted to the image input unit 150 from the camera 151 and stored in the storage unit 120.

Next, in step S142, the control unit 110 extracts feature points of the patient 10 from the image in the image data obtained in step S141, extracts the feature points 15 of the head area of the patient 10 from those feature points in step S143, and calculates positions of the feature points 15 of the head area from past images in step S144.

Returning to FIG. 4, the feature points 15 of the head area of the patient 10 are, as indicated in step S103 of FIG. 3 and as shown in FIG. 4, extracted using a conventional algorithm for extracting feature points of an object (in the present preferred embodiment, the patient 10), after which the positions of the feature points 15 are calculated.

Proceeding to FIG. 8, in step S151, the control unit 110 executes the following processes from step S152 to step S154 for the first movement of the patient.

In step S152, based on the positions calculated in step S144, the control unit 110 calculates the percentage of the feature points 15 of the head area of the patient 10 that have crossed the borderline of the predetermined condition corresponding to that movement. Then, in step S153, the control unit 110 determines whether or not the percentage calculated in step S152 is greater than or equal to a predetermined percentage.

For example, in the case where the patient is moving his or her head, it is determined whether or not the percentage of the feature points 15 that have crossed the borderline 21 that is parallel or substantially parallel to the ends of the bed 20 is greater than or equal to a predetermined percentage (e.g., about 10%), and it is determined that the patient is moving his or her head if the percentage is greater than or equal to the predetermined percentage.

Figure 9:
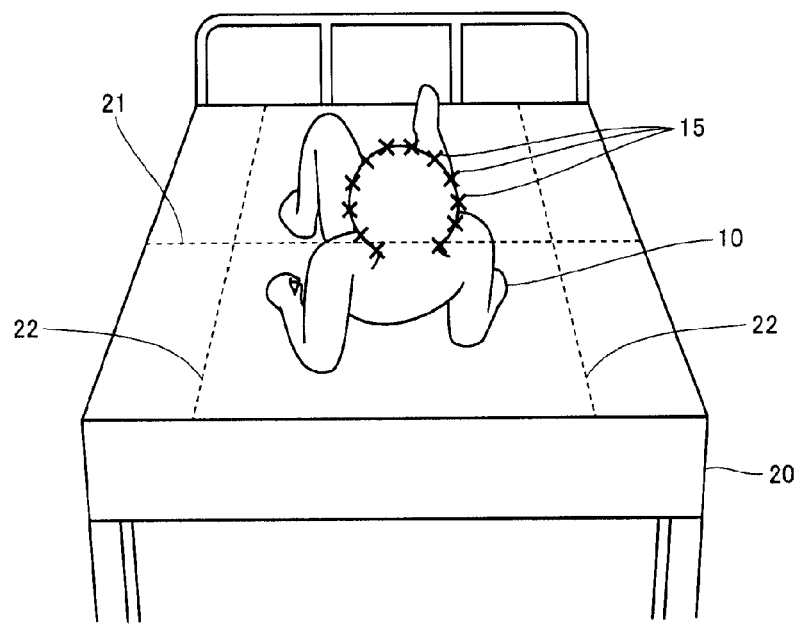
FIG. 9 is a second diagram illustrating an image captured by a camera connected to the control apparatus according to a preferred embodiment of the present invention.

FIG. 9 is a second diagram illustrating an image captured by the camera 151 connected to the control apparatus 100 according to the present preferred embodiment. FIG. 9 illustrates a state in which the patient 10 is partway through an attempt to rise from the bed 20.

In the case where the patient is attempting to rise, it is determined whether or not the percentage of the feature points 15 that have crossed the borderline 21 that is parallel or substantially parallel to the ends of the bed 20 is greater than or equal to a predetermined percentage (e.g., about 50%), and it is determined that the patient is attempting to rise if the percentage is greater than or equal to the predetermined percentage.

In the case where the patient is rising, it is determined whether or not the percentage of the feature points 15 that have crossed the borderline 21 that is parallel or substantially parallel to the ends of the bed 20 is greater than or equal to a predetermined percentage (e.g., about 95%), and it is determined that the patient is rising if the percentage is greater than or equal to the predetermined percentage.

Figure 10:
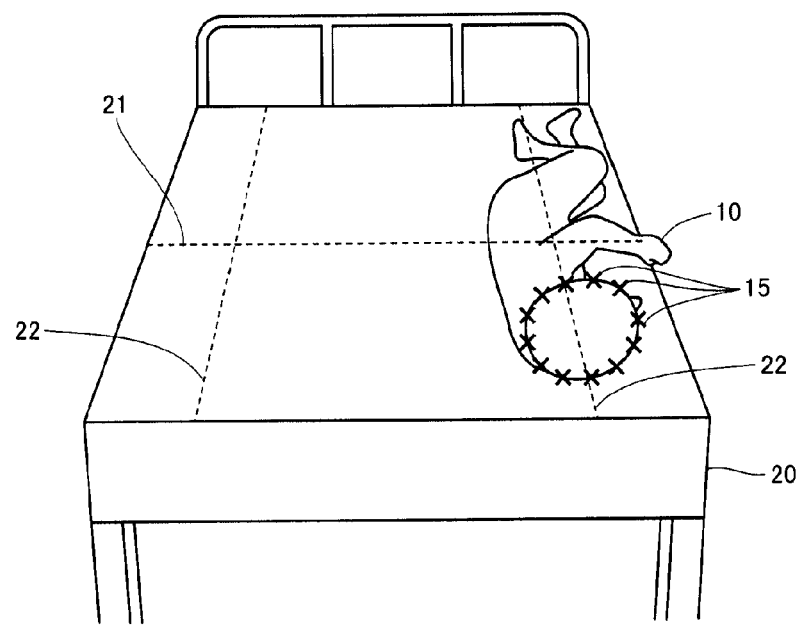
FIG. 10 is a third diagram illustrating an image captured by a camera connected to the control apparatus according to a preferred embodiment of the present invention.

FIG. 10 is a third diagram illustrating an image captured by the camera 151 connected to the control apparatus 100 according to the present preferred embodiment. FIG. 10 illustrates a state in which the patient 10 is partway through an attempt to descend from, or is near falling from, the bed 20.

In the case where the patient is turning over, it is determined whether or not the percentage of the feature points 15 that have crossed the borderline 22 that is parallel or substantially parallel to the sides of the bed 20 is greater than or equal to a predetermined percentage (e.g., about 5%), and it is determined that the patient has turned over if the percentage is greater than or equal to the predetermined percentage.

In the case where the patient is attempting to descend from the bed 20 or is moving in a direction in which the patient will fall from the bed 20, it is determined whether or not the percentage of the feature points 15 that have crossed the borderline 22 that is parallel or substantially parallel to the sides of the bed 20 is greater than or equal to a predetermined percentage (e.g., about 30%), and it is determined that the patient is attempting to descend from the bed 20 or is moving in a direction in which the patient will fall from the bed 20 if the percentage is greater than or equal to the predetermined percentage.

In the case where the patient is descending or falling from the bed 20, it is determined whether or not the percentage of the feature points 15 that have crossed the borderline 22 that is parallel or substantially parallel to the sides of the bed 20 is greater than or equal to a predetermined percentage (e.g., about 95%), and it is determined that the patient is descending or falling from the bed 20 if the percentage is greater than or equal to the predetermined percentage.

In the case where it has been determined that the percentage is greater than or equal to the predetermined percentage (the case where a determination of YES has been made in step S153), in step S154, the control unit 110 communicates the movement of the patient 10 according to the alert level set in step S114 of FIG. 6.

For example, in the case where the alert level is set to "warning" when the patient is attempting to rise, an alert at the level of "warning" communicating that the patient is attempting to rise is made when it has been determined that the patient is attempting to rise.

In the present preferred embodiment, for example, a "warning" that the patient is attempting to rise sounds an alarm, outputs audio indicating that the patient is attempting to rise, flashes a lamp, and displays text indicating that the patient is attempting to rise, for example.

Meanwhile, a "caution" that the patient is attempting to rise outputs audio indicating that the patient is attempting to rise and displays text indicating that the patient is attempting to rise, for example. Finally, a "normal alert" that the patient is attempting to rise displays text indicating that the patient is attempting to rise, for example.

In the case where it has been determined that the percentage of the feature points 15 that have crossed the borderline is not greater than or equal to the predetermined percentage (the case where a determination of NO has been made in step S153), and after step S154, it is determined, in step S155, whether or not a next movement, for which a determination of movement has not yet been made, is being carried out.

In the case where it has been determined that there is a next movement (the case where a determination of YES has been made in step S155), the processes of the aforementioned step S152 to step S154 are executed for that movement. On the other hand, in the case where it has been determined that there is no next movement (the case where a determination of NO has been made in step S155), the process being executed is returned to the process that called this process.

(1-1) As described above, the safe nursing system according to the present preferred embodiment is a system that monitors movements of the patient 10 who is on the bed 20, and includes the control apparatus 100, and the camera 151 that is disposed in a position from which an image including the sides 23 and 23 of the top surface of the bed 20 can be captured.

The control apparatus 100 obtains image data captured by the camera 151; specifies the feature points 15 of an image of the patient 10 in the obtained image data; calculates a value of a predetermined index (for example, coordinates, motion amounts, motion directions, and motion velocities) of the feature points 15 used for specifying a predetermined movement of the patient 10 (for example, the movements illustrated in FIG. 7); sets a predetermined condition to determine a predetermined movement based on the region of the bed 20 in the obtained image data (for example, a condition that the extent to which the coordinates of the feature points 15 have exceeded a predetermined border to determine the predetermined movement has exceeded a predetermined threshold, and a condition that the extent to which the coordinates of the feature points 15 have approached a predetermined border has exceeded a predetermined threshold); determines the predetermined movement based on the calculated values and the set predetermined condition; and, under the condition that it has been determined that the predetermined movement has been made, outputs information indicating that the patient 10 has made the predetermined movement (for example, a warning, a caution, or a normal alert that uses a sound or a display).

In this manner, the camera 151 is disposed in a position from which an image including the sides 23 and 23 of the top surface of the bed 20 can be captured, and thus does not capture images from the side of the bed 20. Accordingly, it is possible to avoid interfering with a caregiver's care.

Furthermore, because the sides 23 and 23 of the top surface of the bed 20 are also captured, a reference value based on the sides 23 and 23 can be set. Accordingly, the degree of danger of movements of the patient 10 can be determined more accurately.

In addition, the movement of the patient 10 is determined not using a range, but by using a plurality of points. For this reason, it is unlikely that errors will appear in the determination results due to differences in the way the patient 10 moves, the body shape of the patient 10, and so on.

The camera 151 is preferably disposed in a position from which an image can be captured from the direction of the head area or the direction of the foot area of the patient 10. Doing so makes it possible to capture an image in which the positional relationship between the patient 10 and the sides 23 and 23 of the bed 20 can easily be understood.

The control apparatus 100 preferably calculates values of predetermined indices of the respective feature points 15 included in a region corresponding to the head area, from among specified feature points. By monitoring movement of the head area in this manner, it is possible to more efficiently monitor the movement of the patient 10 than when monitoring movement in the entire body of the patient 10.

The control apparatus 100 preferably calculates the coordinates of the feature points 15 as the values of the predetermined indices, and sets a condition for predetermined borders (for example, borderlines or border regions) to determine that multiple coordinates indicate a predetermined movement in the patient 10 as the predetermined condition.

The control apparatus 100 preferably determines that the predetermined movement has been made depending on whether or not the degree to which the calculated coordinates exceed the set predetermined border (for example, the percentage of the feature points 15 that have exceeded the border in a predetermined amount of time, the cumulative percentage of the feature points 15 that have exceeded the border) has exceeded a predetermined threshold (for example, a predetermined percentage).

The control apparatus 100 may furthermore determine that the predetermined movement has been made by calculating the direction in which the feature points 15 move as the value of the predetermined index, and determining whether or not the degree to which the calculated coordinates are approaching a predetermined border (for example, the percentage of the feature points 15 that have approached the border within a predetermined amount of time, or the cumulative percentage of the feature points 15 that have approached the border) exceeds a predetermined threshold.

Based on the positions of the sides 23 and 23 or the ends 24 and 24 of the bed 20, the control apparatus 100 sets the predetermined condition in accordance with a pre-set specification method (for example, a method that takes the borderline 21 that is an equal distance from the ends 24 and 24 on the head side and the foot side of the bed 20 as a border to determine that the patient is rising, a method that takes the borderlines 22 and 22 that are equal distances from the center line 25 in the lengthwise direction of the bed 20 and the sides 23 and 23 of the bed 20 as a border to determine that the patient is attempting to move to the side of the bed 20).

The control apparatus 100 preferably sets, for each patient 10, a correspondence relationship (for example, the correspondence relationships indicated in FIG. 7) between a plurality of types of predetermined movements and a plurality of alert levels (for example, "warning", "caution", and "normal alert") based on conditions (for example, poor, fair, and good); calculates values of predetermined indices used to determine a predetermined movement of the patient 10; sets a predetermined condition to determine a predetermined movement; determines the predetermined movement based on the calculated values and the set predetermined condition; and outputs information indicating that the patient 10 has performed the predetermined movement at the alert level indicated by the correspondence relationship set for the patient 10 in accordance with the predetermined movement, under the condition that it has been determined that the predetermined movement has been made.

In this manner, an output indicating that the patient 10 has made a predetermined movement is carried out at an alert level based on the predetermined movement set for each patient 10, and thus a caregiver can be notified based on the condition of each patient 10.

The control apparatus 100 preferably selects and sets the correspondence relationship based on the condition of the patient from among pre-set correspondence relationships between predetermined movements and alert levels set for the respective conditions.

Accordingly, a correspondence relationship between predetermined movements and alert levels can be set more easily based on the condition of the patient 10.

The control apparatus 100 preferably specifies the condition of the patient 10 in accordance with information from an external biological information monitor 200, for example, and selects and sets the correspondence relationship based on the specified condition, from among pre-set correspondence relationships between predetermined movements and alert levels set for the respective conditions.

Accordingly, a correspondence relationship between predetermined movements and alert levels can be set more easily and more objectively based on the condition of the patient 10.

The control apparatus 100 preferably determines whether or not a value indicated by the information from the external biological information monitor 200 has worsened, and in the case where it has been determined that the value has worsened, the control apparatus 100 changes the correspondence relationship so as to raise the alert levels for each of the predetermined movements indicated in the set correspondence relationship.

Through these steps and functions, the settings for the correspondence relationship between the predetermined movements and the alert levels can be changed appropriately in accordance with changes in the condition of the patient, which in turn makes it possible to ensure that notifications that predetermined movements have been made are carried out appropriately based on the situation.

The control apparatus 100 determines whether or not a caregiver is present based on the obtained image data, and in the case where it has been determined that a caregiver is present, the control apparatus 100 changes the correspondence relationship so as to lower the alert levels for each of the predetermined movements indicated in the set correspondence relationship.

Through these steps and functions, the settings for the correspondence relationship between the predetermined movements and the alert levels can be changed appropriately in accordance with whether or not a caregiver is present, which in turn makes it possible to ensure that notifications that predetermined movements have been made are carried out appropriately based on the situation.

The control apparatus 100 may determine whether or not a caregiver is present based on the obtained image data, and in the case where it has been determined that a caregiver is present, may refrain from outputting information.

Doing so makes it possible to avoid making unnecessary alerts in the case where the caregiver is with the patient 10 and alerts indicating that the patient 10 is making a predetermined movement are not necessary.

Next, variations of the aforementioned preferred embodiments of the present invention will be described.

In the aforementioned alert level setting process illustrated in FIG. 6, movements and alert levels preferably are set automatically on a patient-by-patient basis by executing the processes from step S112 to step S114. However, the process is not limited thereto, and specifying the condition as per step S112 and step S113 may be carried out by a doctor or a nurse. Alternatively, the configuration may be such that the movements and alert levels are set on a patient-by-patient basis manually by a doctor or a nurse.

When a person moves, such as when rising, the person's blood pressure value rises. Accordingly, in the case of the patient 10 who is in danger if his or her blood pressure is, for example, 180 mmHg, setting the dangerous blood pressure value of 180 mmHg makes it possible, in step S122 of FIG. 6, to determine that the biological information has worsened in the case where the blood pressure value has reached a value (for example, 160 mmHg) obtained by automatically subtracting a predetermined value (for example, 20 mmHg). The setting may then be changed to raise the alert level before the patient's blood pressure value actually exceeds the dangerous value due to movement such as rising.

In this manner, it may be determined whether or not there is a risk that the biological information will worsen, so that an alert can be made before a dangerous value is actually reached.

In the aforementioned preferred embodiments, the camera 151 preferably is disposed in a position from which an image including both sides 23 and 23 of the top surface of the bed 20 can be captured. However, the position is not limited thereto, and in the case where it is not possible for the patient 10 to fall or descend from one side 23 of the bed, such as when the bed is pushed against a wall or a fall prevention gate is attached thereto, the camera 151 may be disposed in a position from which an image including the other side 23 of the top surface of the bed 20 can be captured.

In the aforementioned preferred embodiments, the borderline is described as a straight line. However, the borderline is not limited thereto, and may be a closed-curve line or an open-curve line, such as a circle, an oval, an arc, or the like. For example, a circle of a predetermined radius from the head area of the patient 10 in FIG. 4 may be taken as the borderline.

Although the aforementioned preferred embodiments describes the camera as being disposed in a predetermined position in the vicinity of the bed 20, no particular mention is made of the position in which the control apparatus 100 is disposed. Rather than being disposed in the vicinity of the bed 20, it may be preferable for the control apparatus 100 to be disposed in a position that is distanced from the bed 20, such as at a nurses' station or the like. Although it is not absolutely necessary to notify a nurse, a caregiver, or the like of the patient's movement when the nurse, caregiver, or the like is near the patient, this configuration makes it possible to notify the nurse, caregiver, or the like that the patient is moving when the nurse, caregiver, or the like is away from the patient and such a notification is highly necessary.

In the aforementioned preferred embodiments, as described in step S154 of FIG. 8, movement of the patient 10 is communicated at the alert level based on that movement using the display unit 140 and the audio output unit 160 of the control apparatus 100 in the safe nursing system. However, the configuration is not limited thereto, and such alerts may be carried out using a different apparatus than the control apparatus 100.

Figure 11:
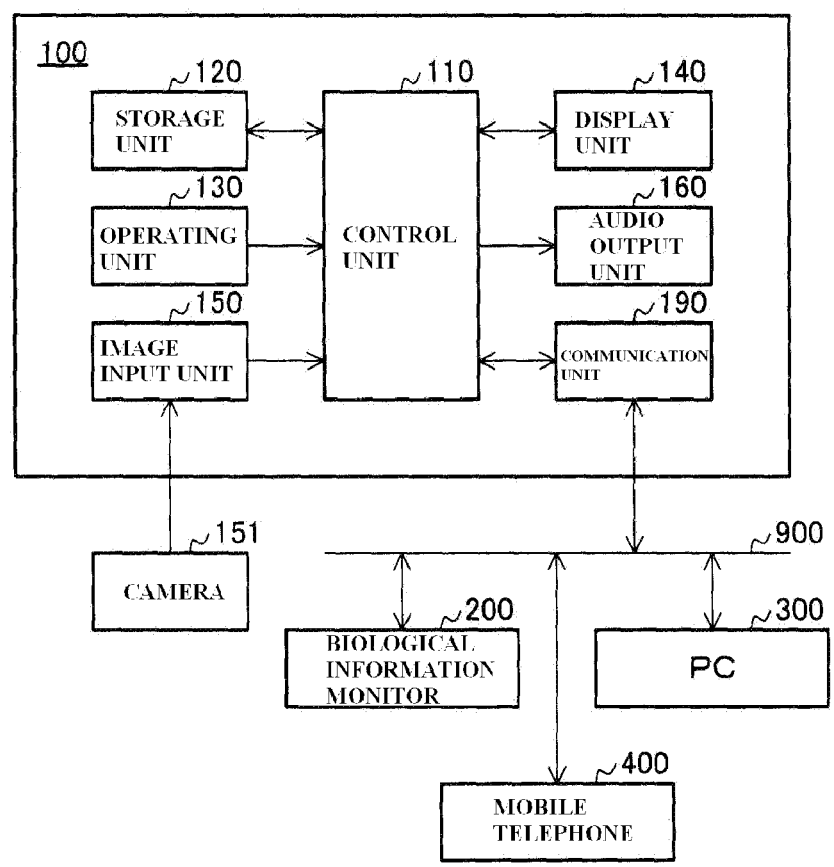
FIG. 11 is a block diagram illustrating the overall configuration of a safe nursing system according to a variation of a preferred embodiment of the present invention.

FIG. 11 is a block diagram illustrating the overall configuration of a safe nursing system according to a variation of the preferred embodiments described above. As shown in FIG. 11, this safe nursing system preferably includes, in addition to the aforementioned configuration, a PC 300 and mobile telephone 400. Alternatively, only one of the PC 300 and the mobile telephone 400 may be included.

The PC 300 and the mobile telephone 400 preferably are connected to the control apparatus 100 via the network 900. Note that the network 900 may include other types of networks, such as a mobile telephone network of a communications carrier, an internal mobile telephone network, or the like.

In this safe nursing system, the control unit 110 of the control apparatus 100 is programmed to control the communication unit 190 to send, to the PC 300 or the mobile telephone 400, information communicating that the patient 10 has moved, at an alert level in accordance with that movement. Based on the received information, the PC 300 or the mobile telephone 400 may then make a notification that the patient 10 has moved, at the alert level that is set in accordance with that movement.

Through these steps and functions, disposing the PC 300 in a position that is distant from the bed 20, such as a nurses' station, makes it possible to notify a nurse, a caregiver, or the like who is away from the patient, and thus requires such a notification, that the patient has moved. Meanwhile, if the nurse, caregiver, or the like carries the mobile telephone 400, the nurse, caregiver, or the like can be notified of the patient's movement even in the case where the nurse, caregiver, or the like is away from the bed 20.

In addition, the nurse, caregiver, or the like in charge of each patient may be set in advance, and a notification that a patient has moved may be made to the mobile telephone 400 carried by the nurse, caregiver, or the like in charge of that patient. According to this configuration, the nurse, caregiver, or the like is only notified of movement of the patients that he or she is in charge of, and is not notified of movement of patients that he or she is not in charge of. Accordingly, unnecessary notifications can be reduced, assisting the nurse, caregiver, or the like in executing appropriate responses.

In the aforementioned preferred embodiments, operating signals to the control unit 110 are inputted from the operating unit 130, as described in FIG. 2. However, the configuration is not limited thereto, and operating signals may be inputted to the control unit 110 of the control apparatus 100 from the PC 300 or the mobile telephone 400 illustrated in FIG. 11.

In the aforementioned preferred embodiments, elements that achieve the functions indicated in the aforementioned flowcharts preferably are configured virtually in the control unit 110 of the control apparatus 100 by the control unit 110 of the control apparatus 100 executing software. However, the configuration is not limited thereto, and the elements that achieve those functions may be configured as and performed by hardware circuits in the control unit 110 of the control apparatus 100.

In the aforementioned preferred embodiments, the safe nursing system and the control apparatus 100 included in the safe nursing system are described as the present invention. However, the present invention is not limited thereto, and can also be achieved as a control method for the safe nursing system or the control apparatus 100 that executes the aforementioned processes using the safe nursing system or the control apparatus 100.

The present invention can also include a control program for the safe nursing system or the control apparatus 100 that executes the aforementioned processes using the safe nursing system or the control apparatus 100.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A safe nursing system comprising:
a control unit programmed to monitor a movement of a patient on a bed, the control unit including:
an image capturing unit disposed in a position from which an image including a side of a top surface of the bed can be captured;
an image capturing control unit programmed to obtain image data captured by the image capturing unit;
a calculation unit that specifies feature points in an image of the patient in the image data obtained by the image capturing control unit, calculates a value of a predetermined index of the feature points used to determine a predetermined movement in the patient, and calculates motion vectors of the feature points;
a setting unit that sets a predetermined condition to determine the predetermined movement based on a region of the bed in the image data obtained by the image capturing control unit, wherein said predetermined condition is set as a cumulative percentage of the motion vectors passing a predetermined borderline to be greater than or equal to a predetermined percentage;
a determination unit that determines the predetermined movement based on the value calculated by the calculation unit and the predetermined condition set by the setting unit; and
an output unit that outputs information indicating that the patient has performed the predetermined movement under the condition that the determination unit has determined that the predetermined movement has been performed.

2. The safe nursing system according to claim 1, wherein the image capturing unit is disposed in a position from which an image can be captured from the direction of a head area of the patient.

3. The safe nursing system according to claim 2, wherein the calculation unit calculates a value of the predetermined index for the feature points included in a region of the head area from among the specified feature points.

4. The safe nursing system according to claim 1, wherein the calculation unit calculates coordinates of the feature points as the value of the predetermined index; and
the setting unit sets, as the predetermined condition, a condition for a predetermined border to determine whether a plurality of the coordinates indicate the predetermined movement in the patient.

5. The safe nursing system according to claim 4, wherein the determination unit determines the predetermined movement based on whether or not an extent to which the coordinates calculated by the calculation unit have exceeded the predetermined border set by the setting unit has exceeded a predetermined threshold.

6. The safe nursing system according to claim 4, wherein the calculation unit further calculates a movement direction of the feature points as the value of the predetermined index; and
the determination unit determines the predetermined movement based on whether or not an extent to which the coordinates calculated by the calculation unit have approached the predetermined border has exceeded a predetermined threshold.

7. The safe nursing system according to claim 1, wherein the setting unit sets the predetermined condition in accordance with a pre-set specification method based on the position of a side or a an end of the bed.

8. A control method for controlling a safe nursing system that includes a control unit and an image capturing unit disposed in a position from which an image including a side of a top surface of a bed can be captured and that monitors a movement of a patient on the bed, the method comprising the steps, executed by the control unit, of:
obtaining image data captured by the image capturing unit;
specifying feature points in an image of the patient in the obtained image data;
calculating a value of a predetermined index of the feature points used to determine a predetermined movement in the patient and motion vectors of the feature points;
setting a predetermined condition to determine the predetermined movement based on a region of the bed in the obtained image data, wherein the predetermined condition is set as a cumulative percentage of the motion vectors passing a predetermined borderline to be greater than or equal to a predetermined percentage;
determining the predetermined movement based on the calculated value and the set predetermined condition; and
outputting information indicating that the patient has performed the predetermined movement under the condition that the predetermined movement has been determined to have been performed.

* * * * *